United States Patent [19]

Wu et al.

[11] 4,166,008
[45] Aug. 28, 1979

[54] PROCESS FOR RECOVERY OF OLEFINIC NITRILES

[75] Inventors: Hsin C. Wu, Parma; William O. Fitzgibbons, Hudson, both of Ohio

[73] Assignee: The Standard Oil Company, Ohio

[21] Appl. No.: 820,479

[22] Filed: Jul. 29, 1977

[51] Int. Cl.² .................... B01D 3/40; C07C 121/32
[52] U.S. Cl. .............................. 203/85; 203/96; 203/98; 203/42; 203/DIG. 3; 203/DIG. 19; 260/465.9
[58] Field of Search .............. 203/DIG. 3, 42, 99, 203/DIG. 19, 71, 78, 79, 84, 85, 92, 93, 95–98; 260/465.9, 465.3

[56] References Cited

U.S. PATENT DOCUMENTS

| 3,149,055 | 9/1964 | Houghland | 260/465.9 |
|---|---|---|---|
| 3,352,764 | 11/1967 | Tyler | 260/465.9 |
| 3,399,120 | 8/1968 | Lovett | 260/465.9 |
| 3,445,347 | 5/1969 | Borrel et al. | 260/465.9 |
| 3,507,755 | 4/1970 | Bitners et al. | 260/465.9 |
| 3,734,943 | 5/1973 | Fitzgibbons et al. | 260/465.9 |
| 3,862,890 | 1/1975 | Presson | 260/465.9 |
| 3,936,360 | 2/1976 | Wu | 203/42 |

Primary Examiner—Wilbur L. Bascomb, Jr.
Attorney, Agent, or Firm—David J. Untener; Herbert D. Knudsen; Larry W. Evans

[57] ABSTRACT

In the recovery and purification of acrylonitrile or methacrylonitrile obtained by the ammoxidation reaction of propylene or isobutylene, the bottoms stream associated with the column for extractively distilling acrylonitrile or methacrylonitrile is both reduced in size and increased in polymer concentration by removing a vapor stream containing water from the lower fourth of said column, thus reducing the amount of solids-containing waste streams to be treated.

12 Claims, 2 Drawing Figures

4,166,008

PROCESS FOR RECOVERY OF OLEFINIC NITRILES

BACKGROUND OF THE INVENTION

Recovery and purification systems for acrylonitrile and methacrylonitrile obtained by the ammoxidation of propylene or isobutylene are well known. See for example U.S. Pat. Nos. 3,433,822; 3,399,120; 3,535,849; and 3,936,360. The gaseous reactor effluent from an ammoxidation reactor is first directly contacted with a quenching liquid to cool the effluent and remove a substantial amount of contaminates produced during the reaction, such as polymers. The cooled gaseous quench effluent is typically sent to a washing column or absorber wherein the gaseous effluent is contacted with water. The liquid stream from the bottom of the absorber containing the various nitriles, water and some impurities is then sent to a distillation column. Solvent water is used to extractively distill this stream, producing an overhead vapor stream of acrylonitrile. As described in U.S. Pat. No. 3,999,120, the bottoms of the extractive distillation column may then be sent to a second stripping column. The overhead of this stripping column contains acetonitrile with a minor amount of water, and the liquid bottoms stream contains water and impurities. An alternate method of recovery, also found in this reference, is the removal of a sidestream from the extractive distillation column. This stream containing mostly acetonitrile and water, is sent to a smaller stripping column with acetonitrile being removed overhead and the liquid bottoms containing mostly water being returned to the extractive distillation column. When this method of recovery is used the liquid bottoms stream from the extractive distillation column is mostly water and impurities with traces of acetonitrile.

Heat necessary to perform the recovery operations is applied to the bottom of both the extractive distillation column and the stripping column. Unfortunately, this heat, usually applied by using an indirect reboiler, brings about polymerization of the impurities found in the associated columns.

Waste disposal of these bottoms streams is both difficult and costly. The solids content of the stream due to the polymerization is so high that it prevents normal waste water treatment. Further, the size of these streams are very large, thus requiring large specialized equipment. For example, German Pat. No. 050,722 discloses a method for purification of this waste water using a separate distillation column and large amounts of steam to evaporate the water, thus reducing the size of the latter specialized waste treatment facilities.

The present invention provides a unique method for reducing the size of these troublesome streams with very little capital investment or operating costs.

SUMMARY OF THE INVENTION

It has now been discovered that in the process for the recovery and purification of acrylonitrile or methacrylonitrile produced by the ammoxidation reaction of propylene or isobutylene, molecular oxygen and ammonia in the presence of ammoxidation catalysts, comprising:
  (a) contacting the ammoxidation reactor effluent containing acrylonitrile or methacrylonitrile, acetonitrile, and impurities with an aqueous quench liquid in a quench system to produce a gaseous quench effluent from said quench system;
  (b) absorbing said gaseous quench effluent in water to form an aqueous solution;
  (c) feeding the aqueous solution to an intermediate tray of a first column having a plurality of trays, using solvent water introduced in the top of said first column to perform a water extractive distillation, wherein a first overhead vapor stream of acrylonitrile or methacrylonitrile with some water is removed from the top of the first column, and a liquid stream containing acetonitrile, impurities and water is removed from the bottom of the first column;
  (d) feeding at least a part of the liquid bottoms from said first column to a second column wherein distillation is performed to remove a second overhead vapor stream of acetonitrile and water from the top of the second column, and a second liquid stream containing water and impurities from the bottom of the second column,
  (e) feeding at least part of the second liquid bottoms stream to the quench system of (a) as the aqueous quench liquid, the improvement comprising: removing a vapor stream from the lower fourth of said second column.

In another embodiment, the invention may be additionally stated as in the process for the recovery and purification of acrylonitrile or methacrylonitrile produced by the ammoxidation reaction of propylene or isobutylene, molecular oxygen and ammonia in the presence of ammoxidation catalysts, comprising:
  (a) contacting the ammoxidation reactor effluent containing acrylonitrile or methacrylonitrile, acetonitrile, and impurities with an aqueous quench liquid in a quench system to produce a gaseous quench effluent from said quench system;
  (b) absorbing said gaseous quench effluent in water to form an aqueous solution;
  (c) feeding the aqueous solution to an intermediate tray of a distillation column having a plurality of trays, using solvent water introduced in the top of said column to perform a water extractive distillation, wherein an overhead vapor stream of acrylonitrile with some water is removed from the top of the column, and a liquid stream containing water and impurities is removed from the bottom of the column.
  (d) removing a first sidestream from the lower half of said column to recover acetonitrile;
  (e) feeding at least a part of the liquid bottoms from said column to the quench system as quench liquid, the improvement comprising: removing a vapor stream containing water from the lower fourth of said column.

The reactor effluent gas, usually at a temperature between 700° and 900° F., is first passed to a quench system. The purpose of the quench system is to remove excess ammonia, polymers and heavier impurities produced by the reaction, and to cool the reactor effluent gas. Typically water with some sulfuric acid is used as a quench liquid. The reactor effluent gas leaves the quench system at a temperature of about 90° to about 230° F. A bottom stream containing water, acid, polymers and other impurities is removed from the quench system. This stream poses very difficult waste disposal problems. Because of the large amount of solids and other impurities in this stream, it cannot be sent to an activated sludge processor or biopond for treatment. Typical methods of treatment in the past have been deep well injection or incineration. As stated in the Background, other methods such as another distillation column have been used in attempts to reduce the size of this stream. It is an object of the present invention to reduce the size of the quench bottom stream and thus reduce the cost of purification.

After being cooled in the quench system, the reactor effluent gases are then passed to an absorber or wash column. Here the effluent gases are contacted with water. The water absorbs acrylonitrile or methacrylonitrile, acetonitrile and some impurities. This aqueous solution is removed from the bottom of the wash column. Non-absorbed gases are removed as a vapor stream from the top of the wash column.

The aqueous solution from the bottom of the absorber is then sent to further processing to recover acrylonitrile and acetonitrile. This processing is normally done in one of two ways.

First, the aqueous solution is sent to an extractive distillation column. This column typically contains 60–120 trays. Solvent water is added to the top of the column and passes countercurrent to the feed. Heat is applied to the bottom of the column, usually by an indirect heat exchanger. Acrylonitrile and HCN are removed as a vapor stream from the top of the column. This stream then goes to further processing to purify the acrylonitrile. Acetonitrile, water and impurities are removed from the bottom of the extractive distillation column and passed to a stripper. In the stripper, large amounts of steam are used to separate the acetonitrile from the water. Acetonitrile is removed as a vapor stream overhead. A bottom stream containing water and impurities is then removed from the stripper and used as the quench liquid in the quench column.

The large amounts of heat necessary to strip the acetonitrile from the water solution also has the undesirable result of polymerizing certain impurities. This polymerization makes waste disposal of the bottom stream extremely difficult.

The present invention greatly reduces the size of the bottom stream by removing a vapor stream from the lower fourth of the stripper. This vapor stream is mainly water with very little if any acetonitrile or impurities. The vapor stream, when condensed, is thus free of solids and hence can be fed to such waste disposal systems as an activated sludge processor or biopond for further treatment. The much reduced bottom stream from the stripper is then sent to the quench column as previously described.

It is preferred that the vapor stream be removed from below the first tray of the column. However, the present invention's vapor stream may be taken from anywhere in the lower fourth of said column.

Where a liquid return is removed from the column as recycle to the acrylonitrile extractive distillation column, the vapor stream should be removed from below this liquid stream.

A second method of purifying the aqueous solution from the absorber is to pass this solution to a somewhat different extractive distillation column. This column, similar to the one previously described, removes a sidestream containing acetonitrile from the lower half of the column. This sidestream is sent to a much smaller stripping column, usually consisting of 20–30 trays. Acetonitrile is removed as an overhead vapor while the liquid bottoms is returned to the extractive distillation column. The bottoms of this modified extractive distillation column is similar to the bottoms stream issuing from the stripper as discussed above. The present invention is also applicable to this method of recovery by removing a vapor stream from the lower fourth of the extractive distillation column. This again has the advantage of greatly reducing the bottoms stream.

DESCRIPTION OF THE DRAWINGS

Referring to FIG. 1, the reactor effluent gas in conduit 100 containing acrylonitrile, HCN, acetonitrile, water vapor and impurities is first passed to a quench column 102. The gas is contacted with quench liquid 130 in the quench column. A bottoms stream containing water and impurities is removed through conduit 106 and sent to waste treatment.

The cooled reactor effluent gases leave the quench system through line 108 and pass as feed to the absorber 110. Wash water enters the absorber at the top through line 112. Non-condensible gases are removed from the absorber through line 114. An aqueous solution containing water, acrylonitrile, acetonitrile and impurities are removed as a bottoms stream through line 116 and passed to the extractive distillation column 118.

Solvent water is introduced to the top of column 118 through line 120 to perform extractive distillation. Acrylonitrile and HCN is removed as an overhead vapor through line 122 and sent to further purification (not shown). A bottoms stream containing acetonitrile and water is removed through line 124 and passed to stripper 126. Heat is added to the stripper to remove acetonitrile as an overhead vapor through line 128. The bottoms stream containing water, polymers and other impurities are removed through line 130 and sent back to the quench system. A vapor stream is removed via line 132 just below the first tray of this column. This vapor stream, containing mostly water, can then be condensed and sent to typical waste treatment facilities such as a sludge processor or biopond. The removal of this vapor stream greatly reduces the amount of water issuing from the bottom of the stripper.

Additionally, a liquid stream may be removed from the lower half of the stripper through line 120 and used as solvent water to the extractive distillation column.

Figure 1:
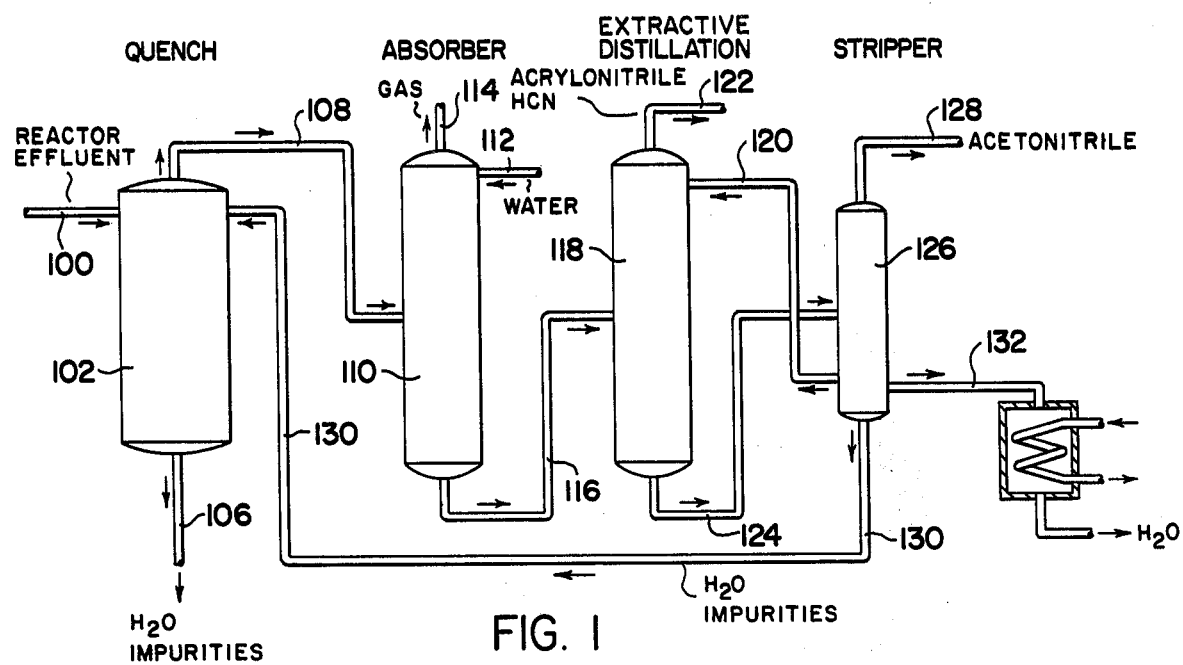
FIGS. 1 and 2 are schematic representations of the present invention as applied to acrylonitrile showing two methods of recovery.
Figure 2:
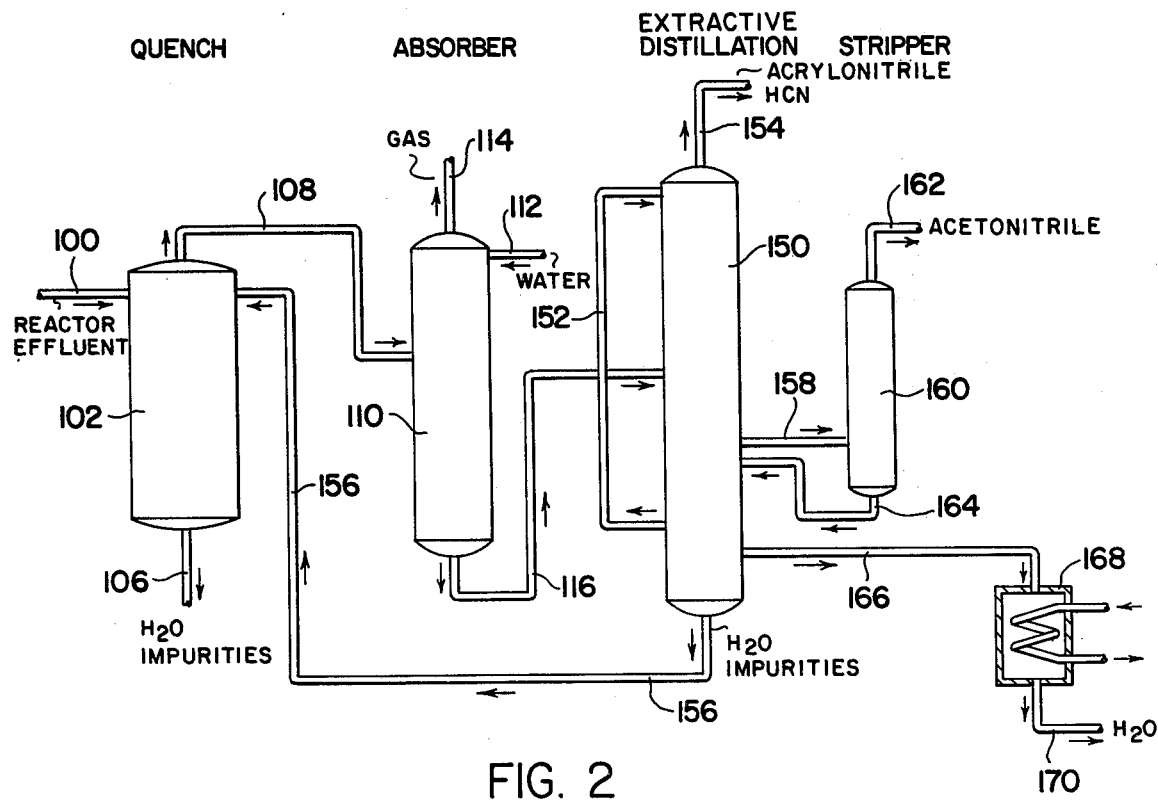

FIG. 2 shows a second embodiment of the invention. The aqueous solution from the absorber 110 is passed through line 116 to a modified extractive distillation column 150. Solvent water is introduced to the top of this column through line 152 to absorb the acetonitrile. Acrylonitrile and HCN is removed overhead as a vapor through line 154. A liquid stream containing acetonitrile and water is removed from the bottom half of this column through line 158 and sent to a small stripping column 160. Acetonitrile passes overhead as a vapor through line 162. A liquid stream containing mostly water is removed from the bottom of column 160 through line 164 and returned to the extractive distillation column. The present invention's vapor stream is removed from below the first tray of the distillation column through line 166 and condensed in condenser 168. The condensed stream containing mostly water is then passed through line 170 to waste treatment as described above.

A bottoms stream containing water, polymers and impurities is removed through line 156 and sent back to the quench system. Additionally, a liquid stream may be removed from the bottommost trays and returned to the extractive distillation column as solvent water through line 152.

DESCRIPTION OF THE PREFERRED EMBODIMENT

Comparative Example A and Example 1

An acrylonitrile recovery process is performed substantially as shown in FIG. 2. In Comparative Example A the total liquid bottoms stream from the extractive distillation column is sent to the quench system. Example 1 is identical to Comparative Example A except that a vapor stream is removed from below the first tray of the extractive distillation column. The amount of this vapor stream was equal to 45% by weight of the original bottoms stream in Comparative Example A. Because of this vapor removal, the amount of heat necessary to perform the distillation was increased by 12%. The Table below shows the weight percent polymer contained in the various process streams of both examples.

TABLE I

Effect of Vapor Removal on Polymer Concentration

| | Wt. % Polymer | | |
|---|---|---|---|
| | Vapor Draw | Column Btms. | Quench Btms. |
| Comp. Example A | — | 1.5 | 10 |
| Example 1 | 0.1 | 2.75 | 24.4 |

As can be seen in this Table, the vapor stream removed from the distillation column contains extremely small amounts of polymer. The effects of the present invention can easily be seen by the dramatic increase in polymer concentration in the quench bottoms stream. This concentration of polymer has been doubled through the use of the invention. Additionally, the quench bottoms stream is reduced by approximately 60%. Thus a much smaller stream more highly concentrated in polymer is obtained. This has the advantage of greatly reducing the cost and further disposal of this stream.

The amount of vapors that may be removed when using the present invention is related to the bottoms stream of the column. The amount of vapors removed can be 10 to about 70 weight percent of the bottoms stream prior to vapor removal. It is preferred, however, that 30–50 weight percent be removed. This will leave a sufficient quantity of water for use in the quench system.

As stated previously, the vapor stream can be condensed and because of its extremely low polymer concentration be sent to typical waste water purification systems such as a biopond or activated sludge treatment.

The use of the present invention greatly reduces the amount of quench bottoms to be purified and also increases its polymer concentration. This makes waste treatment of this stream far more economical and reduces the size of the associated equipment.

We claim:

1. In the process for the recovery and purification of acrylonitrile or methacrylonitrile produced by the ammoxidation reaction of propylene or isobutylene, molecular oxygen and ammonia in the presence of ammoxidation catalysts, comprising:
   (a) contacting the ammoxidation reactor effluent containing acrylonitrile or methacrylonitrile, acetonitrile, and impurities with an aqueous quench liquid in a quench system to produce a gaseous quench effluent from said quench system;
   (b) absorbing said gaseous quench effluent in water to form an aqueous solution;
   (c) feeding the aqueous solution to an intermediate tray of a distillation column having a plurality of trays, using solvent water introduced in the top of said column to perform a water extractive distillation, wherein an overhead vapor stream of acrylonitrile or methacrylonitrile with some water is removed from the top of the column, and a liquid stream containing water and impurities is removed from the bottom of the column;
   (d) removing a first sidestream from the lower half of said column to recover acetonitrile;
   (e) feeding at least a part of the liquid bottoms from said column to the quench system as quench liquid, the improvement comprising:
   removing a vapor stream containing water substantially free of polymers from the lower fourth of said column.

2. The process of claim 1 wherein the vapor stream is removed from below the first tray of said column.

3. The process of claim 2 wherein the vapor stream is condensed after being removed from said column.

4. The process of claim 2 including the step of removing a second liquid stream from the lower fourth of said column and using said second stream as the solvent water to the column.

5. In the process for the recovery and purification of acrylonitrile or methacrylonitrile produced by the ammoxidation reaction of propylene or isobutylene, molecular oxygen and ammonia in the presence of ammoxidation catalysts, comprising:
   (a) contacting the ammoxidation reactor effluent containing acrylonitrile or methacrylonitrile, acetonitrile, and impurities with an aqueous quench liquid in a quench system to produce a gaseous quench effluent from said quench system;
   (b) absorbing said gaseous quench effluent in water to form an aqueous solution;
   (c) feeding the aqueous solution to an intermediate tray of a first column having a plurality of trays, using solvent water introduced in the top of said first column to perform a water extractive distillation, wherein a first overhead vapor stream of acrylonitrile or methacrylonitrile with some water, is removed from the top of the first column, and a liquid stream containing acetonitrile, impurities and water is removed from the bottom of the first column;
   (d) feeding at least a part of the liquid bottoms from said first column to a second column wherein distillation is performed to remove a second overhead vapor stream of acetonitrile and water from the top of the second column, and a second liquid stream containing water and impurities from the bottom of the second column,
   (e) feeding at least part of the second liquid bottoms stream to the quench system of (a) as the aqueous quench liquid, the improvement comprising: removing a vapor stream containing water substantially free of polymers from the lower fourth of said second column.

6. The process of claim 5 wherein the vapor stream is removed from below the first tray of said second column.

7. The process of claim 6 wherein the vapor stream is condensed after being removed from the second column.

8. The process of claim 6 including the step of removing a liquid stream from the lower fourth of the second column and using this stream as the solvent water to the first column in said step (a).

9. The process of claim 1 wherein the amount of the vapor stream removed is 10 to about 70 weight percent of the liquid stream of step (c).

10. The process of claim 1 wherein the amount of the vapor stream removed is 30 to about 50 weight percent of the liquid stream of step (c).

11. The process of claim 4 wherein the amount of the vapor stream removed is 10 to about 70 weight percent of the second liquid stream of step (d).

12. The process of claim 4 wherein the amount of the vapor stream removed is 30 to about 50 weight percent of the second liquid stream of step (d).

* * * * *